United States Patent [19]

Hummel-Marquardt et al.

[11] Patent Number: 5,700,666
[45] Date of Patent: Dec. 23, 1997

[54] PROCESS FOR THE PRODUCTION OF ARABINONUCLEOTIDES

[75] Inventors: Heidi Hummel-Marquardt; Thomas Schmitz; Mario Kennecke; Alfred Weber, all of Berlin, Germany

[73] Assignee: Schering Aktiengesellschaft, Berlin, Germany

[21] Appl. No.: 619,548

[22] PCT Filed: Sep. 6, 1994

[86] PCT No.: PCT/EP94/02949

§ 371 Date: Sep. 4, 1996

§ 102(e) Date: Sep. 4, 1996

[87] PCT Pub. No.: WO95/09244

PCT Pub. Date: Apr. 6, 1995

[30] Foreign Application Priority Data

Sep. 28, 1993 [DE] Germany ............... 43 33 727.9

[51] Int. Cl.$^6$ ............... C12P 19/40; C12N 1/20
[52] U.S. Cl. ............... 435/88; 536/26.3; 536/267.1; 536/27.4; 536/27.61; 536/27.63; 435/822; 435/824; 435/829; 435/850; 435/874
[58] Field of Search ............... 435/88, 874, 829, 435/850, 824, 822; 544/277, 251; 536/26.3, 27.61, 27.63, 26.71, 27.4

[56] References Cited

U.S. PATENT DOCUMENTS 5,180,824  1/1993  Bauman et al. ............ 536/26.71
5,602,246  2/1997  Bauman et al. ............ 536/26.3

OTHER PUBLICATIONS

Patent Abstract Japan Band 5, No. 152 C-75 JP 56-82098 Jul. 4, 1981 (Ajinomoto KK).
Patent Abstract Japan Band 7 No. 219 C-188 JP58-116698 Jul. 11, 1983 (Ajinomoto KK).

*Primary Examiner*—Herbert J. Lilling
*Attorney, Agent, or Firm*—Millen, White, Zelano, & Branigan, P.C.

[57] ABSTRACT

A process for the production of arabinonucleotides of general formula I

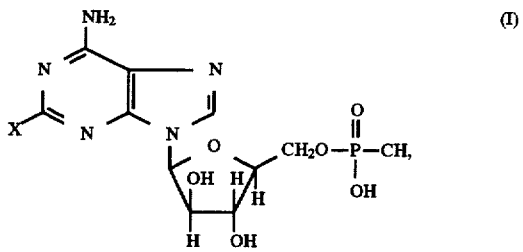

(I)

in which

X represents a hydrogen atom or a fluorine atom, is described, which is characterized in that an arabinonucleoside of general formula II

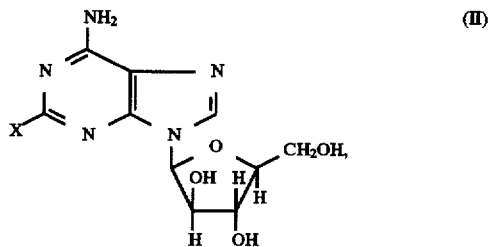

(II)

in which X has the above-mentioned meaning, is fermented in the presence of an aryl phosphate of general formula III

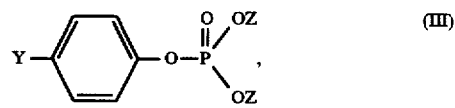

(III)

in which

Y symbolizes a hydrogen atom or a nitro group and
Z symbolizes two hydrogen atoms or two alkali metal atoms, with a microorganism that is capable of phosphorylating nucleosides.

5 Claims, No Drawings

PROCESS FOR THE PRODUCTION OF ARABINONUCLEOTIDES

The invention relates to a process for the production of arabinonucleotides of general formula I

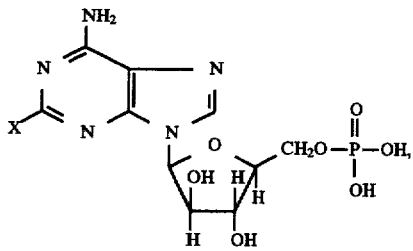

in which
X represents a hydrogen atom or a fluorine atom, which is characterized in that an arabinonucleoside of general formula II

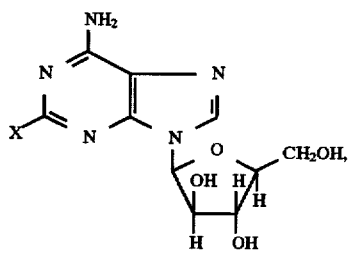

in which X has the above-mentioned meaning, is fermented in the presence of an aryl phosphate of general formula III

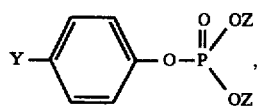

in which
Y symbolizes a hydrogen atom or a nitro group and
Z symbolizes two hydrogen atoms or two alkali metal atoms,
with a microorganism that is capable of phosphorylating nucleosides.

As is generally known, the arabinonucleotides of general formula I, 9(5-0-phosphono-β-D-arabinofuranosyl)-9-H-purine-6-amine (=vidarabine phosphate) and 2-fluoro-9-(5-0)-phosphono-β-D-arabinofuranosyl)-9H-purine-6-amine (=fludarabine phosphate), are pharmacologically effective substances that are distinguished by an antiviral and cyclostatic action (EP-A 317,728 and WO 9209604).

According to the known processes, these compounds are produced by phosphorylation of the corresponding nucleosides (Bull. of th. Chem. Soc. Japan 42, 1969, 3505–3508, New Journal of Chem. 11, 1987, 779–785 and WO 9209604). In this process, heavily contaminated crude products, whose purification is very expensive and lossprone, are obtained.

The process according to the invention makes it possible to synthesize these substances in a relatively simple way in a considerably more pure form than that which is possible by means of the previously known processes.

This is surprising to one skilled in the art. Although from the studies by Koji Mitsugi et al. (Agr. Biol. Chem. 28, 1964, 586–600), it has already been known for a long time that the nucleoside inosine can be microbiologically phosphorylated, it had to be expected that basically less advantageous results would be achieved when the nucleosides of general formula II were phosphorylated. This is the case especially for two reasons: From the works of Koji Mitsugi et al., it is known that mixtures of isomeric nucleotides are often obtained in the phosphorylation of inosine. It was to be expected, consequently, that when the nucleosides of general formula II were phosphorylated, isomeric mixtures would be obtained to the same extent—if not to an even greater extent.

It is known that during metabolism adenosine is degraded, with deamination and oxidation (Römpps Chemie-Lexikon, 8th ed, Frankch Publishing House, Stuttgart (DE) 65), and it was accordingly to be feared that during the microbiological reaction of the adenine derivatives of general formula II, degradation of the compounds would also occur, at least partially.

As separate tests, which with the microorganism *Pseudomonas trifolii* that is also mentioned by Koji Mitsugi et al. (according to a study of the DSM-identification service, IAM 1309 is now classified as Pantoeaagglomerans), the above-mentioned feared drawbacks in the case of the phosphorylation of the nucleosides of general formula II do not occur; rather, the reaction seems to proceed even more advantageously than that of inosine.

It is highly probable that the process according to the invention can be carried out not only with the tested microorganism *Pseudomonas trifolii* (IAM 1309), but also with other microorganisms, which are described by Koji Mitsugi et al. as suitable for phosphorylation of nucleosides. These are, for example, the microorganisms:

| | |
|---|---|
| *Pseudomonas trifolii* | IAM 1543 and IAM 1555 |
| *Pseudomonas perlurdia* | IAM 1589, IAM 1600, IAM 1610 and IAM 1627, |
| *Pseudomonas melanogenum* | F-11, |
| *Alcaligenes visco lactis* | ATCC 9039 and IFM AN-14, |
| *Achromobacter superficialis* | IAM 1433 |
| *Flavobacterium lactis* | IFM F101 |
| *Flavobacterium fuscum* | IAM 1181 |
| *Flavobacterium flavescens* | IFO 3085 |
| *Flavobacterium breve* | IFM S-15 |
| *Serracina marcescens* | IAM 1022, IAM 1065, IAM 1067, IAM 1104, IAM 1135, IAM 1161, IAM 1205, IAM 1223, IAM 1703 | and other microorganisms which are cited in this publication.

To achieve adequate phosphorylation of the arabinonucleosides of general formula II that can be produced only at very great expense, the process according to the invention must be carried out in the presence of a large excess of a phosphate donor. Suitable phosphate donors are, i.a., aryl phosphates, such as phenyl phosphate or p-nitrophenyl phosphate. Usually, 2–5 mol of phosphate donor is used per mol of nucleoside to be reacted.

Since the proteases that occur in bacteria are, in most cases, alkaline proteases, which produce zinc proteins, and require, in most cases, magnesium ions to exert their action, it is sensible to carry out the reaction in the presence of 0.2 to 4.0% of a water-soluble zinc salt, such as, for example, zinc sulfate dihydrate or optionally also in the presence of 0.01 to 0.3% of a water-soluble magnesium salt, such as magnesium sulfate-heptahydrate.

Apart from the above-mentioned conditions, the process according to the invention can be carried out under the same conditions as are commonly used in the fermentation of substrates with bacteria cultures. The bacteria culture is cultivated in a suitable medium to which substrate and adjuvants are added, and the culture is fermented while being stirred and aerated until maximum substrate conversion is accomplished.

If this process is used, generally fermentation broths in which the process product can be separated from the fermentation medium only with difficulty are obtained.

It therefore generally seems more sensible to carry out the reaction under the conditions of the resting-cell process. For this purpose, the bacteria cultures are cultivated in a standard medium, the bacteria are separated by centrifuging, washed, optionally freeze-dried—to make them storable—resuspended in an isotonic buffer solution, mixed with substrate and adjuvants, and fermented at 20° to 40° C. until maximum substrate conversion is accomplished. Under these conditions the working-up of the batch causes no difficulties, the cell material is centrifuged off, the supernatant is concentrated by evaporation, and the precipitated process product, which can be contaminated by easily separable starting material, is filtered off.

The following embodiments are used to explain the process according to the invention:

EXAMPLE 1 a) A Petri dish with a medium that contains

| | |
|---|---|
| 1% | peptone |
| 0.2% | yeast extract |
| 0.1% | magnesium sulfate-heptahydrate and |
| 1.5% | agar | set at pH 7.0
is inoculated with a dry culture of *Pseudomonas trifolii* IAM 1309 and incubated for 16 hours at 30°.

b) A 2 l Erlenmeyer flask with 1 l of medium that contains

| | |
|---|---|
| 1% | peptone |
| 0.2% | yeast extract and |
| 0.1% | magnesium sulfate-heptahydrate | set at pH 7
is inoculated by means of a loop with the preliminary culture that is produced according to a) and incubated for 16 hours at 30° C. at 180 rpm. Then, the cells are centrifuged off for 15 minutes at 6000 rpm at 10° C., washed with 200 ml of a 0.02% aqueous potassium chloride solution, suspended in 20 ml of a 0.02% aqueous potassium chloride solution, frozen at −20° C. and freeze-dried for 20 hours. For use, the freeze-dried cells are stored at room temperature.

c) Into threaded flasks,

| | |
|---|---|
| 2.0 g | of 2-fluoro-9-(β-D-arabonofuranosyl)-9H-purine-6-amine, |
| 0.12 g | of zinc sulfate-dihydrate, |
| 1.0 g | of freeze-dried Pseudomonat trifolii IAM 1309 culture that is produced according to Example 1b and |
| 8.0 g | of disodium-p-nitrophenyl phosphate | are introduced in 0.5M sodium acetate buffer of pH 4.5 per liter, and the reaction mixture is shaken for 40 hours at 40° C. at 60 rpm.

Then, the cells are centrifuged off at 8000 rpm, the supernatant is concentrated by evaporation in a rotary evaporator to 1/20 of the original volume at a maximum of 50° C., and the separated crude product is filtered out, washed with water, and dried for 24 hours at 100° C. and 10.000 Pa.

According to HPLC [high-pressure liquid chromatography] analysis of the crude product obtained, about 50% of 2-fluoro-9-(5-0-phosphono-β-D-arabinofuranosyl)-9H-purine-6-amine was formed in this test.

EXAMPLE 2

Under the conditions of Example 1, but with the addition of 16 g/l of disodium-p-nitrophenyl phosphate instead of 8 g/l, 2.0 g/l of 2-fluoro-9(β-D-arabinofuranosyl)-9H-purine-6-amine is shaken for 40 hours at 40° C. at 60 rpm. The working-up of the reaction mixture is carried out as described in Example 1c, and about 60% of 2-fluoro-9-(5-0-phosphino-β-D-arabinofuranosyl)-9H-purine-6-amine is obtained.

EXAMPLE 3

Under the conditions of Example 1c, but also with the addition of 40 g/l of disodium-p-nitrophenyl phosphate instead of 8 g/l, 2.0 g/l of 2-fluoro-9(β-D-arabinofuranosyl)-9H-purine-6-amine is shaken for 100 hours at 40° C. at 60 rpm. The working-up of the reaction mixture is carried out as described in Example 1c, and about 85% of 2-fluoro-9-(5-0-phosphono-β-D-arabinofuranosyl)-9-H-purine-6-amine is obtained.

EXAMPLE 4

Under the conditions of Example 1c, but with the addition of 20 g/l of disodium phenyl phosphate instead of 8 g/l of disodium-p-nitrophenyl phosphate, 2.0 g/l of 2-fluoro-9(β-D-arabinofuranosyl)-9H-purine-6-amine is shaken for 100 hours at 40° C. at 60 rpm. The working-up of the reaction mixture is carried out as described in Example 1c, and about 50% of 2-fluoro-9-(5-0-phosphono-β-D-arabinofuranosyl)-9H-purine-6-amine is obtained.

EXAMPLE 5

Under the conditions of Example 4, but with the addition of 30 g/l of disodium-phenyl phosphate instead of 20 g/l, 2.0 g/l of 2-fluoro-9-(β-D-arabinofuranosal)-9H-purine-6-amine is reacted, worked up, and 60% of 2-fluoro-9-(5-0-phosphono-β-D-arabinofuranosyl)-9H-purine-6-amine is obtained.

EXAMPLE 6

Under the conditions of Example 4, but with the addition of 40 g/l of disodium-phenyl phosphate instead of 20 g/l, 2.0 g/l of 2-fluoro-9-(β-D-arabinofurynosyl)-9H-purine-6-amine is reacted, worked up, and 70% of 2-fluoro-9-(5-0-phosphono-β-D-arabinofuranosyl)9-H-purine-6-amine is obtained.

We claim:

1. A process for the production of an arabinonucleotide of formula I

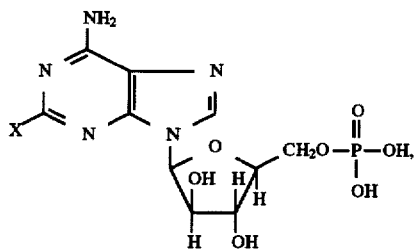 (I)

wherein:

X is a hydrogen atom or a fluorine atom, comprising, fermenting an arabinonucleoside of formula II

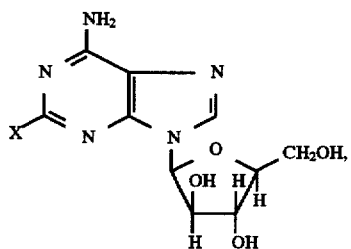 (II)

wherein X has the above-mentioned meaning, in the presence of an aryl phosphate of formula III

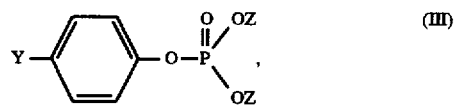 (III)

where

Y is a hydrogen atom or a nitro group; and

Z is two hydrogen atoms or two alkali metal atoms, with a microorganisms that is capable of phosphorylating nucleosides.

2. A process for the production of arabinonucleotides of formula I according to claim 1, wherein the fermentation is carried out in the presence of a water-soluble zinc(II) salt.

3. A process for the production of arabinonucleotides of formula I according to claim 1, wherein the fermentation is carried out under the conditions of the resting cell process.

4. A process for the production of arabinonucleotides of formula I according to claim 1, wherein a microorganism of the species *Pseudomonas trifolii* is used for fermentation.

5. A process for the production of arabinonucleotides of general formula I according to claim 1, wherein a microorganism of the species *Pseudomonas trifolii* IAM 1309 is used for fermentation.

* * * * *